United States Patent [19]

Liu et al.

[11] Patent Number: 5,549,907
[45] Date of Patent: *Aug. 27, 1996

[54] IONOMERIC SUTURE AND ITS METHOD OF MANUFACTURE

[75] Inventors: Cheng-Kung Liu, Norwalk; John C. Brewer, Bristol, both of Conn.

[73] Assignee: United States Surgical Corporation, Norwalk, Conn.

[ * ] Notice: The term of this patent shall not extend beyond the expiration date of Pat. No. 5,284,489.

[21] Appl. No.: 184,362

[22] Filed: Jan. 19, 1994

Related U.S. Application Data

[63] Continuation of Ser. No. 944,595, Sep. 14, 1992, abandoned.

[51] Int. Cl.$^6$ .............................. A61F 13/00; A61K 9/70
[52] U.S. Cl. .......................... 424/443; 606/139; 606/77; 606/154; 606/228
[58] Field of Search .................... 424/443; 526/348.1; 525/362; 606/148, 139, 144, 154, 228

[56] References Cited

U.S. PATENT DOCUMENTS

| | | | |
|---|---|---|---|
| 3,054,406 | 9/1962 | Usher | 606/151 |
| 3,124,136 | 3/1964 | Usher | 606/213 |
| 3,264,272 | 8/1966 | Rees | 428/36.9 |
| 3,322,734 | 5/1967 | Rees | 525/328.5 |
| 3,404,134 | 10/1968 | Rees | 525/362 |
| 3,630,205 | 12/1971 | Listner | 606/231 |
| 3,849,185 | 11/1974 | Shepherd et al. | 424/443 |
| 4,172,820 | 10/1979 | Lundberg et al. | 524/401 |
| 4,193,137 | 3/1980 | Heck | 3/1.4 |
| 4,226,751 | 10/1980 | Lundberg et al. | 260/23.5 |
| 4,259,284 | 3/1981 | Lundberg et al. | 264/184 |
| 4,343,859 | 8/1982 | Lundberg et al. | 428/364 |
| 4,347,847 | 9/1982 | Usher | 128/334 R |
| 4,452,245 | 6/1984 | Usher | 128/334 R |
| 4,520,821 | 6/1985 | Schmidt et al. | 128/334 R |
| 4,633,873 | 1/1987 | Dumican et al. | 128/334 R |
| 4,652,264 | 3/1987 | Dumican et al. | 623/1 |
| 4,655,221 | 4/1987 | Deuerux | 128/334 R |
| 4,838,884 | 6/1989 | Dumican et al. | 604/364 |
| 4,983,180 | 1/1991 | Kawai et al. | 606/228 |
| 5,002,551 | 3/1991 | Linsky et al. | 606/151 |
| 5,006,267 | 4/1991 | Vaughn et al. | 210/755 |
| 5,147,382 | 9/1992 | Gertzman et al. | 606/228 |
| 5,147,383 | 9/1992 | Bezwada et al. | 606/228 |

FOREIGN PATENT DOCUMENTS 0436514  4/1991  European Pat. Off. .

OTHER PUBLICATIONS

European Patent Office Search Report.

*Primary Examiner*—Thurman K. Page
*Assistant Examiner*—William E. Benston, Jr.

[57] ABSTRACT

An ionomer suture exhibits excellent properties. The suture may be monofilament or multifilament, and methods of making and using the suture are disclosed.

8 Claims, 2 Drawing Sheets

5,549,907

IONOMERIC SUTURE AND ITS METHOD OF MANUFACTURE

This is a continuation of application Ser. No. 07/944,595, filed on Sep. 14, 1992, abandoned.

BACKGROUND OF THE INVENTION

This invention relates to medical devices formed totally or in part from an ionomeric resin, and more particularly to a suture fabricated from an ionomer resin as well as to a melt extrusion (spinning) process for fabricating the filament.

It is well known that nonabsorbable sutures can be manufactured from various nonionic thermoplastic resins such as polyolefins, polyesters, polyamides, poly(esteramides), copolyether amides, polyether-polyester block copolymers, and polyurethane block copolymers.

Ionomer resins are known, inter. alia, from U.S. Pat. Nos. 3,264,272, 3,322,734 and 3,404,134. Fibers manufactured from ionomer resins employing a wet or dry spinning process are known from U.S. Pat. Nos. 4,172,820, 4,226,751, 4,259,284 and 4,343,859. The fibers have use in clothing, carpeting and similar applications.

Commonly owned copending U.S. patent application Ser. No. 07/932,377, now U.S. Pat. No. 5,284,489, describes both fibers and sutures fabricated from blends of non-ionic thermoplastic resin and ionomer resins.

SUMMARY OF THE INVENTION

In accordance with the present invention there are provided both monofilmnent and multifilament sutures manufactured from at least one ionomer resin. It is, of course, within the scope of the present invention to utilize blends or copolymers of two or more ionomers in the resins from which sutures of the present invention are obtained.

In another aspect of the present invention there is provided a process for manufacturing an ionomer suture comprising the operations of extruding ionomer resin at an extrusion temperature of from about 70° C. to about 230° C. to provide a monofilament fiber, stretching the solidified monofilament at a temperature of from about 30° C. to about 90° C. in water (or other suitable liquid medium) or at from about 40° C. to about 120° C. in air (or other suitable gaseous medium) at a stretch ratio of from about 3:1 to about 7:1 to provide a stretched monofilament. The stretched monofilament optionally may be annealed with or without relaxation at a temperature of from about 40° C. to about 120° C. to provide the finished suture.

The ionomer resin component of the suture of the present invention advantageously possesses the ability to bond with bioactive substances such as cationic biocidal agents thus providing an effective and convenient device for the long term release of such substances at or near the wound site.

In addition, the suture of this invention exhibits reduced strain energy compared with that of a known non-absorbable thermoplastic suture (e.g. an all-polyolefin suture) strain energy being defined as the integration of the measured stress-strain curve for a monofilament measured in kilograms-mm and is equivalent to the work expended in elongating the monofilmnent by a specified percentage of its original length. The strain energy of a monofilament suture is related to the amount of effort required to straighten the suture upon removal of the suture from its package such that the lower the strain energy the lesser the effort required to straighten the suture prior to use.

DESCRIPTION OF THE PREFERRED EMBODIMENTS

Figure 1:
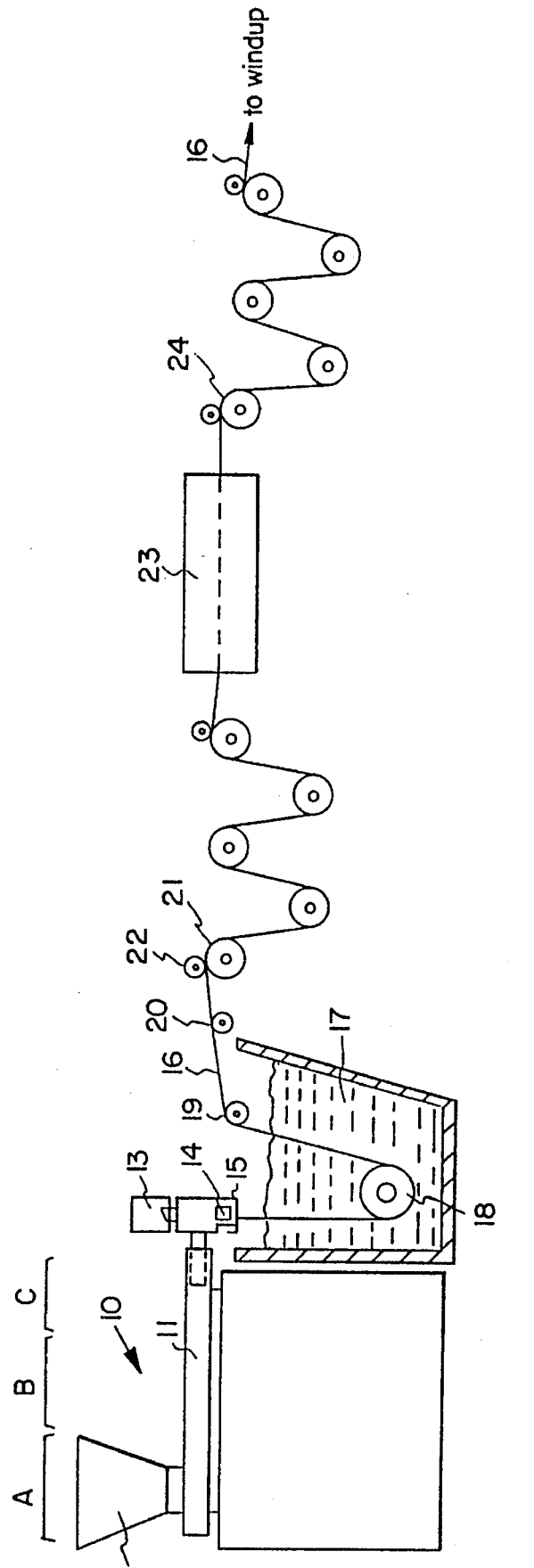
FIG. 1 is a schematic illustration of apparatus which is suitable for manufacturing the monofilmnent suture of this invention; and, FIG. 2 is a perspective view of a suture of the present invention attached to a needle.

Suitable ionomer resins from which sutures of the present invention are made are biologically compatible, ionically cross-linked thermoplastic resins generally prepared by neutralizing a copolymer containing pendent acid groups, e.g., carboxylic acid groups, sulfonic acid groups and/or phosphonic acid groups, with an ionizable metal compound, e.g., a compound of the monovalent, divalent and/or trivalent metals of Groups I, II, IV-A and VIII-B of the Periodic Table of Elements. See, "Encyclopedia of Polymer Science and Engineering", 2nd Edition, Vol. 8, pp. 393–423 (John Wiley & Sons, 1987), the contents of which are incorporated by reference herein.

A preferred group of ionomer resins is derived from a copolymer of at least one alpha-olefin and at least one ethylenically unsaturated carboxylic acid and/or anhydride. Suitable alpha-olefins include ethylene, propylene, butane-1, pentane-1, hexene-1, heptene-1,3-methylbutene, and the like. Suitable carboxylic acids and anhydrides include acrylic acid, methacrylic acid, ethacrylic acid, maleic acid, fumaric acid, maleic anhydride, and the like. The foregoing copolymer advantageously contains from about 0.2 to about 20 mole percent, and preferably from about 0.5 to about 10 mole percent, carboxylic acid groups. Particular examples of such copolymers include ethylene/acrylic acid copolymers, ethylene/methacrylic acid copolymers, ethylene/itaconic acid copolymers, ethylene/methyl hydrogen maleate copolymers, ethylene/maleic acid copolymers, ethylene/acrylic acid/methyl methacrylate copolymers, ethylene/methacrylic acid/ethylacrylate copolymers, ethylene/itaconic acid/methyl methacrylate copolymers, ethylene/methyl hydrogen maleate/ethyl acrylate copolymers, ethylene/methacrylic acid/vinyl acetate copolymers, ethylene/acrylic acid copolymers, ethylene/acrylic acid/vinyl alcohol copolymers, ethylene/acrylic acid/carbon monoxide copolymers, ethylene/propylene/acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinylidene chloride/acrylic acid copolymers, ethylene/vinyl fluoride/methacrylic acid copolymers, and ethylene/chlorotrifluoroethylene/methacrylic acid copolymers. The copolymers may also, after polymerization but prior to ionic crosslinking, be further modified by various reactions to result in polymer modifications which do not interfere with their subsequent ionic crosslinking. Halogenation of an olefin acid copolymer is an example of such polymer modification.

The preferred ionomer resins are obtained by reacting the foregoing copolymers with a sufficient amount of metal ions as to neutralize at least about 5 percent by weight, and preferably from about 20 to about 100 percent by weight, of the carboxylic acid groups present. Suitable monovalent metal ions include $Na^+$, $K^+$, $C^+$, $Rb^+$, $Hg^+$, and $Cu^+$. Suitable divalent ions include $Be^{+2}$, $mg^{+2}$, $Ca^{+2}$, $Sr^{+2}$, $Ba^{+2}$, $Cu^{+2}$, $Cd^{+2}$, $Hg^{+2}$, $Sn^{+2}$, $Pb^{+2}$, $Co^{+2}$, $Ni^{+2}$, and $Zn^{+2}$. Suitable trivalent metal ions include $Al^{+3}$, $Sc^{+3}$, $Fe^{+3}$, and $Y^{+3}$.

The preferred metals suitable for neutralizing the copolymers used herein are the alkali metals, particularly cations such as sodium, lithium and potassium, and alkaline earth metals, in particular, cations such as calcium, magnesium and zinc.

Ionomer resins of the preferred type are disclosed, inter alia, in U.S. Pat. Nos. 3,264,272, 3,322,734 and 3,404,134, the contents of which are incorporated by reference herein. Ionomer resins derived from ethylene/methacrylic acid copolymers, e,g., DuPont's Surlyn® resins, are particularly preferred. Surlyn® resins 8020 and 8920 provide especially good results. It is, of course, within the scope of the present inventions to utilize two or more ionomer resins to form sutures described herein.

The suture of the present invention is fabricated from at least 40% by weight, preferably at least 60% by weight and most preferably at least 90% by weight of ionomer resin. One or more optional ingredients can be incorporated into the ionomer resin. Such optional ingredients include biologically compatible, plasticizers, antioxidants, stabilizers, fillers, colorants, bioactive substances such as biocidal agents, antibiotics, growth factors, anti-clotting agents medicinal agents including drugs, enzymes, proteins, peptides, glycoproteins, or diagnostic agents such as releasable dyes which may have no biological activity per se.

Examples of classes of medicinal agents that can be used in accordance with the present invention include antimicrobials, analgesics, antipyretics, anesthetics, antiepileptics, antihistamines, anti-inflammatories, cardiovascular drugs, diagnostic agents, sympathomimetic, cholinomimetic, antimuscarinics, antispasmodics, hormones, growth factors, muscle relaxants, adrenergic neuron blockers, anti-neoplastics, immunosuppressants, gastrointestinal drugs, diuretics, steroids and enzymes and combinations thereof. A particularly advantageous group of optional ingredients are those bioactive substances that areicapable of being ionically bonded to one or both resin components of the blend, e.g., as disclosed in U.S. Pat. No. 5,006,267, the contents of which are incorporated by reference herein. Bioactive substances having this capability include cationic biocidal agents such as acetyl trimethyl mrunonium bromide, alkyltrimethyl ammonium chloride, monoalkyldimethyl benzyl ammonium salts, heteroaromatic ammonium salts, bio-quaternary salts, and the like.

Sutures may be prepared by melt extruding (spinning) an ionomer resin to provide a monofilament, cooling the monofilament, stretching the cooled monofilament to effect orientation of the resin molecules and annealing (relaxing) the oriented monofilament.

In general, the conditions of the individual steps of extruding, stretching and annealing may be substantially the same as those disclosed in U.S. Pat. No. 3,630,205. Similarly, the process may employ much the same type apparatus as that described in U.S. Pat. No. 3,630,205.

A suitable process for the manufacture of monofilament sutures of the present invention comprises the operations of melt extruding the ionomer resin at an extrusion temperature of from about 70° C. to about 230° C. to provide a monofilament, stretching the solidified monofilament at a temperature of from about 30° C. to about 90° C. in water (or other suitable liquid medium) or at from about 40° C. to about 120° C. in air (or other suitable gaseous medium) at a stretch ratio of from about 3:1 to about 7:1 to provide a stretched monofilament. Optionally, the monofilament may then be annealed at a temperature of from about 40° C. to about 120° C. to provide the finished suture, the annealing resulting in shrinkage of the stretched monofilament for a recovery to within about 75 to about 97 percent of the length of the monofilament prior to annealing.

FIG. 1 schematically illustrates the extrusion and stretching operations of the resin blend filament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of the ionomer resin are introduced to the extruder through drier-hopper 12. Motor driven metering pump 13 delivers extruded resin at a constant rate to spin pack 14 and thereafter through spinneret 15 possessing one or more orifices of desired diameter to provide a molten filament 16 which then enters quench bath 17, e.g., containing water, where the filament solidifies. The distance filament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling of the monofilament in some unpredictable manner. In general, barrel zone A of the extruder can be maintained at a temperature of from about 70° to 120° C., zone B at from about 80° to 150° C. and zone C at from about 100° to about 180° C. Additional temperature parameters include: metering pump block 13 at from about 140° to about 200° C., spin pack 14 at from about 140° to about 200° C., spinneret 15 at from about 160° to about 210° C. and quench bath 17 at from about 25° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sized 4/0 to 8/0, monofilament 16 is drawn through heating unit 23, which can be an oven chamber or a hot water trough, by means of second godet 24 which rotates at a higher speed than first godet 21 thereby stretching the monofilament from three to seven time its original length. Where heating unit 23 is an oven chamber, its temperature is advantageously maintained at from about 40° to about 100° C. and preferably from about 60° to about 80° C. In the case of larger sutures, e.g., sizes 2 to 3/0, it is preferred that heating unit 23 be a hot liquid trough or bath such as a water or glycerol bath which is maintained at a temperature of from about 30° to about 90° C.

For smaller suture sizes, e.g., sizes 6/0 to 8/0, the monofilament optionally can be passed through a second heating unit, e.g., maintained at a temperature of from about 50° to about 120° C. and preferably from about 60° to about 80° C., by means of a hot air oven to heat-treat the monofilament prior to the annealing operation. This second heat treatment results in on-line relaxation, or shrinkage, of the monofilament, e.g., for a recovery of from about 85 to about 97%, and preferably from about 90 to about 95%, of the stretched length of the monofilament. In order to accommodate this on-line shrinkage in the monofilament, the third godet is driven at a speed which is somewhat less than that of the second godet.

In the larger suture sizes, e.g., sizes 5/0 and larger, (when desired) annealing is accompanied by shrinkage of the suture, e.g., for a recovery of from about 75 to about 95%, and preferably from about 85 to about 92% of its stretched length.

In carrying out the annealing operation, the desired length of suture can be wound around a creel and the creel placed in a heating cabinet maintained at the desired temperature, e.g., as described in U.S. Pat. No. 3,630,205. After a suitable period of residency in the heating cabinet, e.g., about 10 to 30 minutes or so, the suture will have undergone shrinkage, e.g., to about 90% of the stretched length for sutures of sizes 2 to 3/0, to about 95% of the stretched length for sutures of sizes 4/0 and 5/0 and essentially no shrinkage in the case of sutures of sizes 6/ to 8/0. As shown in U.S. Pat. No. 3,630,206, the creel can be rotated within the heating cabinet in order to insure uniform heating of the monofilament or the cabinet can be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Multifilament sutures of the present invention may be made by methods well known in the art. Braid constructions such as those disclosed in U.S. Pat. Nos. 5,059,213, 5,019,093 and 4,959,069 are suitable for the multi filament sutures of the present invention. The suture can be coated or filled with substances which improve its functional characteristics, e.g., its lubricity, its knot tie down properties, etc. Similarly, the suture can be coated with one or more substances which enhance its usefulness as a wound closure device, e.g., with any of the bioactive substances previously mentioned.

Figure 2:
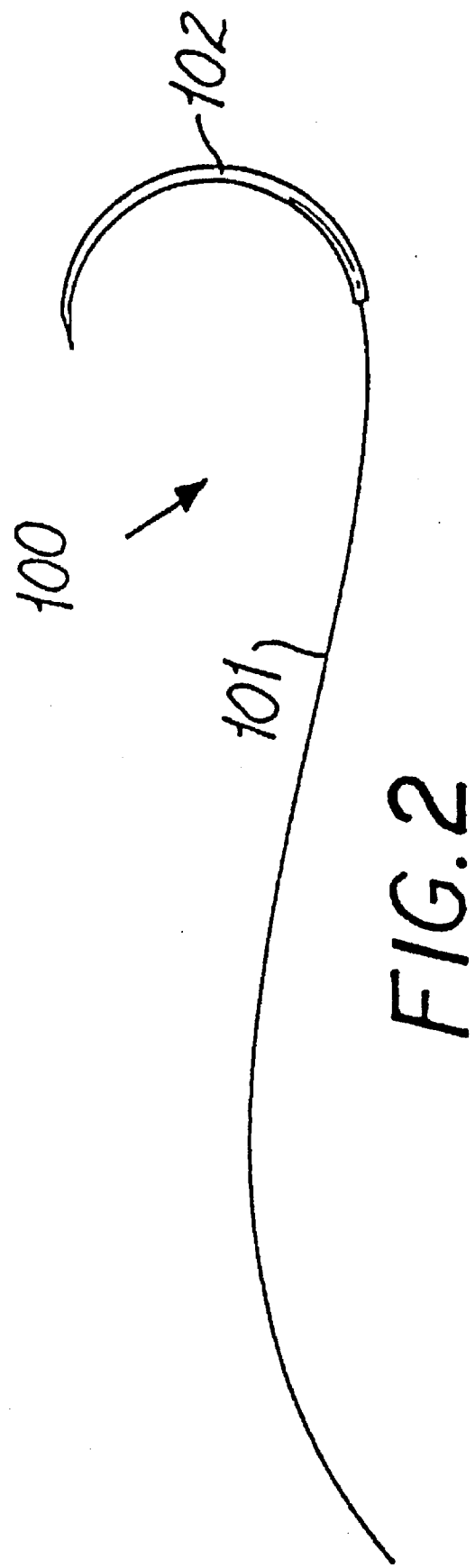

The suture of the present invention, suture 101, may be attached to a surgical needle 102 to form device 100 as shown in FIG. 2 by methods well known in the art. Suturing with combined suture-surgical device 100 is accomplished in accordance with accepted surgical practice, i.e., with repeated passes of needle 102 through approximated tissue at the wound site to ligate the wound followed by tying a knot in the suture and removing the needle.

In order that those skilled in the art may be better able to practice the present invention, the following examples are given as an illustration of the preparation and characteristics of the ionomeric sutures of the present invention. It should be noted that the invention is not limited to the specific details embodied in the examples.

EXAMPLE

Table I below set forth typical conditions for the extruding, stretching and annealing operations used in manufacturing the suture of this invention. The individual resins employed were Surlyn® 8020 ionomer resin.

TABLE I

| MONOFILAMENT SUTURE MANUFACTURING CONDITIONS | |
| --- | --- |
| Suture Size | 3/0 |
| Process Conditions | Extrusion Operation |
| extruder screw, rpm | 3.7 |
| metering pump rpm | 8.6 |

TABLE I-continued

| MONOFILAMENT SUTURE MANUFACTURING CONDITIONS | |
| --- | --- |
| barrel temp., °C., zone A | 90 |
| barrel temp., °C., zone B | 100 |
| barrel temp., °C., zone C | 140 |
| clamp temp., °C. | 140 |
| adapter temp., °C. | 140 |
| pump temp., °C. | 170 |
| block temp., °C. | 170 |
| spinneret, °C. | 185 |
| barrel pressure psi, | 3000 |
| metering pump pressure, psi | 1650 |
| spinneret pressure., psi | 1600 |
| metering pump size, cc/rev. | 0.584 |
| diameter of orifices, mm | 1.25 |
| quench bath temp., °C. | 30 |
| Process Conditions | Stretch (Orientation) Operation |
| draw bath temp., °C. | 60 |
| first godet speed, mpm | 6.0 |
| second godet speed, mpm | 24.4 |
| draw ratio | 4:1 |
| Process Conditions | Annealing (Relaxation) Operation |
| Third Godet Speed mpm | 23.7 |
| oven temp., °C. | 60 |
| shrinkage % | 97 |

The average physical properties of the sutures and the procedures employed for their measurement are set forth in Table II as follows:

TABLE II

| PROCEDURES FOR MEASURING PHYSICAL PROPERTIES OF IONOMERIC MONOFILAMENT SUTURES | |
| --- | --- |
| Physical Property | Test Procedure |
| knot-pull, strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength nonabsorbable sutures (n = 10 loops per group). The loop is placed next to a cloth-wrapped mandrel rotating at .5 rpm. The fixtures are secured to allow contact of the cloth material against the fourth, i.e. top throw of each knot. The cloth wrapping is moistened with 37° C. water prior to the test and is periodically remoistened during the test. Each pass of the cloth across the knot (for a total of 100 passes), the knot is inspected for top throw security. For a knot to be considered secure, the 3 mm ears must not come undone and there must be no relaxation of the knot or loss of the fourth throw. |

Table III below sets forth the physical properties of the size 3/0 ionomeric suture of the present invention.

TABLE III

| Physical Property | |
| --- | --- |
| diameter (mm) | 0.249 |
| knot-pull strength (kg) | 0.78 |
| Straight-pull strength (kg) | 0.9 |
| Strain Energy 0–5% (kg-mm) | 0.84 |
| Strain Energy 0–10% (kg-mm) | 3.94 |
| Elongation (%) | 34 |
| Tensile Strength (kg/mm$^2$) | 20 |
| Knot Security* | 0/10 |

*Number of knot failures out of 10 samples tested to 100 cycles.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A size 3/0 monofilament suture comprising a filament spun from a composition containing at least about 30 mole percent an ionomeric copolymer of at least one alpha olefin and at least one member selected from the group of ethylenically unsaturated carboxylic acid and ethylenically unsaturated carboxylic acid anhydride, the suture exhibiting a maximum 0–5% strain energy of about 2 kg-mm.

2. A suture fabricated from a composition comprising at least one ionomer resin having at least one bioactive substance ionically bonded to the ionomer resin.

3. A medical device comprising a needle-suture combination comprising an ionomeric suture having at least one bioactive substance ionically bonded to the ionomeric suture.

4. A medical device comprising a size 3/0 monofilament suture-needle combination comprising a filament spun from a composition containing an ionomeric resin the suture exhibiting a maximum 0–5% strain energy of about 2 kg-mm.

5. The suture of claim 4 wherein the size 3/0 monofilament suture exhibits a knot-pull strength of about 0.8 kg.

6. The suture of claim 4 wherein the size 3/0 monofilament exhibits a straight-pull strength of about 0.9 kg.

7. A medical device comprising a suture-needle combination comprising a size 3/0 filament spun from a composition containing an ionomeric resin, the suture being of multifilament construction and exhibiting a 0–5% strain energy of about 2 kg-mm.

8. The suture of claim 1 wherein the ionomer copolymer is based on a copolymer of ethylene and methacrylic acid.

* * * * *